(12) United States Patent
Maier et al.

(10) Patent No.: US 11,903,869 B2
(45) Date of Patent: Feb. 20, 2024

(54) EASILY REMOVABLE PESSARY DEVICE

(71) Applicant: Reia, LLC, Lyme, NH (US)

(72) Inventors: Kaitlin E. Maier, Darien, CT (US); Ariana M. Sopher, Somerville, MA (US); Meegan P. Daigler, Portland, ME (US)

(73) Assignee: Reia, LLC, Lyme, NH (US)

( * ) Notice: Subject to any disclaimer, the term of this patent is extended or adjusted under 35 U.S.C. 154(b) by 546 days.

(21) Appl. No.: 17/210,576

(22) Filed: Mar. 24, 2021

(65) Prior Publication Data

US 2021/0228404 A1    Jul. 29, 2021

Related U.S. Application Data

(63) Continuation-in-part of application No. 16/832,839, filed on Mar. 27, 2020, now Pat. No. 11,491,047, which is a continuation-in-part of application No. 16/141,955, filed on Sep. 25, 2018, now Pat. No. 11,185,438.

(60) Provisional application No. 63/000,791, filed on Mar. 27, 2020, provisional application No. 62/563,443, filed on Sep. 26, 2017, provisional application No. 62/827,230, filed on Apr. 1, 2019.

(51) Int. Cl.
*A61F 6/08*    (2006.01)
*A61F 6/14*    (2006.01)
*A61F 6/12*    (2006.01)

(52) U.S. Cl.
CPC ........................... *A61F 6/12* (2013.01)

(58) Field of Classification Search
CPC ...... A61F 6/06; A61F 6/08; A61F 6/12; A61F 6/14; A61F 2/06; A61F 2/0022; A61F 2/004; A61F 2/005; A61F 2/0036; A61F 2/0031
See application file for complete search history.

(56) References Cited

U.S. PATENT DOCUMENTS

| 2,422,377 | A | | 6/1947 | Waterbury | |
| 3,626,942 | A | | 12/1971 | Waldron | |
| 3,756,228 | A | * | 9/1973 | Lerner | A61F 6/148 |
| | | | | | 128/839 |
| 3,937,217 | A | * | 2/1976 | Kosonen | A61F 6/144 |
| | | | | | 128/839 |
| 4,579,110 | A | * | 4/1986 | Hamou | A61F 6/225 |
| | | | | | 128/831 |
| 4,677,967 | A | | 7/1987 | Zartman | |
| 5,014,722 | A | | 5/1991 | Bauer | |

(Continued)

FOREIGN PATENT DOCUMENTS

| GB | 1121925 A | 7/1968 |
| JP | 06133996 A | 5/1994 |

(Continued)

*Primary Examiner* — Camtu T Nguyen
(74) *Attorney, Agent, or Firm* — Hinckley, Allen & Snyder, LLP; David R. Josephs

(57) ABSTRACT

A pessary device has a support portion, a stem and a loop attached to the stem to facilitate manipulation and control of the pessary device. The loop portion is flexible and provides a hole for receipt of a finger of the person inserting or removing the pessary device. The loop portion preferably includes a taper and/or a dimpled end to facilitate the use of a finger or an applicator for insertion of the device deeper into the vagina.

30 Claims, 10 Drawing Sheets

(56) References Cited

U.S. PATENT DOCUMENTS

| | | |
|---|---|---|
| 6,503,190 B1 | 1/2003 | Ulmsten et al. |
| 6,530,879 B1 | 3/2003 | Adamkiewicz |
| 6,645,137 B2 | 11/2003 | Ulmsten et al. |
| 8,127,768 B2 | 3/2012 | Ziv |
| 8,302,608 B2 | 11/2012 | Harmanli |
| 8,651,109 B2 | 2/2014 | Ziv et al. |
| 8,728,013 B2 | 5/2014 | Perle et al. |
| 8,840,598 B2 | 9/2014 | Minoguchi et al. |
| 8,888,676 B2 | 11/2014 | Ziv et al. |
| 8,911,344 B2 * | 12/2014 | Altan ............... A61F 2/005 600/30 |
| 8,919,345 B2 | 12/2014 | Avery, Jr. et al. |
| 8,926,493 B2 | 1/2015 | Karapasha |
| 9,078,726 B2 | 7/2015 | Karapasha |
| 9,211,211 B2 | 12/2015 | Maurette |
| 9,320,640 B2 | 4/2016 | Durling et al. |
| 9,339,364 B2 | 5/2016 | Durling et al. |
| 9,393,090 B2 | 7/2016 | Karapasha |
| 9,402,703 B2 | 8/2016 | Ziv et al. |
| 9,433,523 B2 | 9/2016 | Avery, Jr. et al. |
| 9,439,748 B2 | 9/2016 | Durling et al. |
| 9,555,168 B2 | 1/2017 | Browning |
| 9,597,222 B2 | 3/2017 | Durling et al. |
| 9,649,219 B2 | 5/2017 | Strong et al. |
| 9,655,769 B2 | 5/2017 | Ziv et al. |
| 9,717,582 B2 | 8/2017 | Arcand et al. |
| 9,744,630 B2 | 8/2017 | Avery, Jr. et al. |
| 10,039,666 B2 | 8/2018 | Ziv et al. |
| 10,143,598 B2 | 12/2018 | Strong et al. |
| 10,188,545 B2 | 1/2019 | Conti |
| 10,201,411 B2 | 2/2019 | Ramachandran et al. |
| 10,335,312 B2 | 7/2019 | Williams et al. |
| 10,405,959 B2 | 9/2019 | Ziv |
| 10,617,503 B2 | 4/2020 | Rosen et al. |
| 2009/0266367 A1 | 10/2009 | Ziv |
| 2013/0025604 A1 | 1/2013 | Harmanli |
| 2013/0327338 A1 * | 12/2013 | Churchill ............ A61F 6/144 128/833 |
| 2016/0235583 A1 | 8/2016 | Durling et al. |
| 2017/0100278 A1 | 4/2017 | Ziv et al. |
| 2017/0224457 A1 | 8/2017 | Strong et al. |
| 2018/0296387 A1 | 10/2018 | Ziv et al. |
| 2018/0296388 A1 | 10/2018 | Ziv et al. |
| 2019/0053937 A1 | 2/2019 | Meyer |
| 2019/0091062 A1 | 3/2019 | Sopher et al. |
| 2019/0336260 A1 * | 11/2019 | Price ..................... A61F 6/08 |

FOREIGN PATENT DOCUMENTS

| | | |
|---|---|---|
| SU | 1680154 A1 * | 9/1991 |
| WO | 2004103213 A1 | 12/2004 |
| WO | 2008079271 A1 | 7/2008 |
| WO | 2017064713 A1 | 4/2017 |
| WO | 2020205614 A1 | 10/2020 |

* cited by examiner

EASILY REMOVABLE PESSARY DEVICE

CROSS REFERENCE TO RELATED APPLICATION

This application claims the benefit of, and priority from, U.S. Provisional Application No. 63/000,791, entitled "EASILY REMOVABLE PESSARY DEVICE," filed Mar. 27, 2020, the entirety of which is incorporated by reference herein.

This application is additionally a continuation-in-part of co-pending U.S. patent application Ser. No. 16/832,839, entitled PESSARY FOR PELVIC ORGAN PROLAPSE, filed Mar. 27, 2020, which is a continuation-in-part of co-pending U.S. patent application Ser. No. 16/141,955, entitled PESSARY FOR PELVIC ORGAN PROLAPSE, filed Sep. 25, 2018, which claims the benefit of U.S. Provisional Application Ser. No. 62/563,443, entitled PESSARY FOR PELVIC ORGAN PROLAPSE, filed Sep. 26, 2017, and also claims the benefit of U.S. Provisional Application Ser. No. 62/827,230, entitled PESSARY FOR PELVIC ORGAN PROLAPSE, filed Apr. 1, 2019, each of which applications are incorporated herein by reference.

GOVERNMENT LICENSE RIGHTS

This invention was made with government support under a Phase I Small Business Innovation Research grant awarded by the National Institute of Health, grant application ID: 1 R43 HD097809-01 and a Phase II Small Business Innovation Research grant awarded by the National Institute of Health, grant application ID: 2 R44 HD097809-02. The government has certain rights in the invention.

BACKGROUND OF THE INVENTION

This invention relates to pessaries for use in treating pelvic organ prolapse (POP), and more specifically, to removable pessaries.

About 50 percent of women over the age of 50 suffer from some degree of pelvic organ prolapse. The female pelvic organs include the bladder, uterus, vagina, and rectum. A prolapse is a medical condition in which at least one organ of the body has collapsed forward, backward, or downward. Pelvic organ prolapse can result from weakening of the pelvic floor muscles and loss of integrity of the pelvic floor connective tissue, which allows for abnormal uterine or vaginal descent. In certain cases, the uterus or portions of the vagina can descend through the opening to the vagina. Symptoms of pelvic organ prolapse include pelvic discomfort, difficulty with urinating and voiding, and sexual dysfunction.

Contributory factors for pelvic organ prolapse can include a history of pregnancy and childbirth, advanced age, smoking, obesity, connective tissue disorders upper respiratory disorders, repetitive strain injuries, and neuropathies. The severity of pelvic organ prolapse can range from minor and asymptomatic to more severe degrees requiring medical intervention. In the latter case, women can choose to undergo reconstructive surgery using a surgically implanted mesh or a native tissue repair to resuspend the fallen structures. As an alternative to surgery, women can manage their prolapse with a pessary. The present invention is directed to such a pessary device for non-surgical management of pelvic organ prolapse.

FIG. 1 of the prior art presents a case of pelvic organ prolapse in which certain of the pelvic organs have descended from a female pelvic region 100. The female pelvic region 100 is shown in a side view such that the front side 102 is oriented to the left and the rear side 104 is to the right. The pelvic region 100 is supported by a skeletal frame 106. A plurality of prolapsed organs 108 have descended from the pelvic region below the pelvic floor axis 109 that corresponds to a plane running from front to rear along the bottom of the pelvic region. Ordinarily, the pelvic organs are disposed above axis 109. The prolapsed organs 108 that have descended below axis 109 to include a bladder 110, a uterus 112 and the vagina 114. In the case of the vagina 114, this organ has become inverted, such that the interior lining is now an exterior surface, to the great discomfort of the person for whom it is an ordinary recessed organ. A rectum 116 remains situated above axis 109, but it is contemplated that eventually, it can descend through axis 109 to join the other prolapsed organs 108.

A pessary is a device that can be inserted into the vagina to support the descending organs. Pessaries can be recommended for women who do not wish to undergo surgery, for pregnant women, or for women with other serious health issues which makes surgery too risky. Pessaries are primarily made of medical grade silicone, with some containing internal plastic support structures for added rigidity. Some pessaries are entirely or partially made of acrylic. In function, the pessary resides in the vaginal canal and provides support for the descending organs.

For example, the pessary device of FIG. 2A, as shown inserted in FIG. 3, is a known attempt in the prior art to manage and treat pelvic organ prolapse, commonly known as a "Gellhorn" pessary. This prior art pessary 200 is inserted into the vagina 114 to support the prolapsed organs 108 of FIG. 1. The pessary 200 can be placed in the vagina 114 just above axis 109 and can stay in place due to residual tone of the pelvic floor muscle group 202 and at least one of a suction, a friction force, and/or larger size (so as to cause the vaginal wall to indent around the perimeter of the pessary 200). When in position, the pessary 200 supports the organs above it and prevents them from impinging upon or passing through the vaginal introitus (opening) 204.

However, pessaries can cause erosion of the vaginal lining (epithelium) if they are inappropriately sized or left in situ for prolonged periods. To fit a pessary, a healthcare practitioner (for example, a physician, a physician's assistant, a nurse, or midwife) assesses the size of the vaginal introitus 204 and depth. The pessary can be lubricated, inserted, and positioned behind the pubic symphysis 206, which is a bony structure in the skeletal frame 106. As shown in FIGS. 2A and 2B, the prior art Gellhorn type pessary 200 is a simple device including a ring 220, a stem 222, and a knob 224, and is inserted as shown in FIG. 3. Pessaries in the prior art tend to be rigid and difficult to remove and re-insert by the user alone. Many women return to the practitioner every three to six months to have their pessary removed, cleaned, and replaced. Some women are able to remove and clean their pessaries themselves. The recommendations for self-cleaning have not been standardized globally; but for example, current Canadian practice advises any woman who is able to remove her own pessary to remove, wash, and replace it once per week. Pessaries can be cumbersome and uncomfortable to insert and remove. The average pessary user is a postmenopausal woman and these women often experience vaginal atrophy and dryness as well as narrowing of the vaginal canal and introitus, creating the potential for further difficulty and discomfort of insertion and removal. Currently available pessaries are manually folded or compressed to some degree before insertion. Although this can be helpful with enhancing the ease and comfort of the insertion, currently available pessaries are not able to significantly decrease in cross-sectional area. During removal it can be difficult to fold the pessary, often resulting in the pessary being removed in its full or close to full size and shape, which causes discomfort and difficulty. These attributes make self-maintenance of the pessary very painful, if not impossible, and consequently, few women with a pessary are able to remove, clean, and insert their own pessaries. Furthermore, some pessaries are not removable by the patient at all.

Therefore, existing pessary devices in the prior art suffer from being not easily removable and, therefore, may not address an important need for the non-surgical management and treatment of pelvic organ prolapse. While the ring 220 with support pessary (as shown in FIG. 2B) of the prior art does contain holes to allow for drainage of fluids, the holes can also be used by patients and physicians as a feature to grab for increased leverage during removal. However, the holes are located within the body of the ring pessary, making them difficult to reach. The Gellhorn prior art device has a protruding stem 222 with a knob 224, however, the stem 222 is more for alignment once in place than it is for removal. The knob 224 is relatively small in diameter. The vast majority of patients are unable to grasp the stem 222 for removal and practitioners often need to use forceps to grip the knob 224 for removal. When the pessary 200 is lubricated to attempt to minimize the pain and tearing with insertion, or when it is lubricated after having been in the vagina, this further increases the difficulty of holding the pessary during both insertion and removal.

Even when pessaries are handled by a skilled practitioner, the process of removal can often be painful. Practitioners have described using forceps, that they conceal from view of the patient, to grip and remove the pessary. It can be difficult to get the proper leverage to pull out the pessary, often resulting in pain and potential tearing for the patient.

Beyond general irritation that is caused by the pessary as a foreign object in the body, the protruding, rigid knob 224 on the existing stem can result in a pressure point when in constant contact with the vaginal wall leading to irritation, pressure sores and, in extreme cases, fistulas into the bladder or rectum.

The relative rigidity of pessaries and the difficulties in removal can result in a reliance on a healthcare practitioner for regular cleaning, an inability to experience vaginal intercourse, and the pessary remaining inserted even when not necessary. It is desirable for a pessary to be readily inserted and removed by the user, thereby improving the quality of life for that user.

Therefore, there is still a need to manage and treat pelvic organ prolapse non-surgically with a pessary, which is, as stated above, a medical device that is inserted into the vagina and acts as a shelf to support the descending organs. Due to their fixed and rigid design, current state of the art pessaries are difficult or impossible to remove and insert independently by patients. Consequently, women must rely on physicians for regular pessary cleanings, may have difficulties engaging in sexual intercourse, and must wear their pessary even when not necessary, increasing a woman's risk of developing ulcers and other avoidable complications associated with long term wear.

Moreover, a pessary that better enables self-maintenance additionally increases accessibility to prolapse management. In under resourced areas, where access to the frequent medical care needed for prolapse maintenance is difficult, a pessary that enables users to remove it and clean it themselves increases opportunity for treatment.

Therefore, there is a particular need for a pessary device that can be inserted and removed easily by the non-medically trained user without the assistance of a medical practitioner.

SUMMARY OF THE INVENTION

The present invention preserves the advantages of prior art pessary devices while additionally providing new advantages not found in currently available pessaries and overcomes many disadvantages of such currently available pessaries.

The pessary of the present invention overcomes the disadvantages of the prior art by providing a pessary that can be readily inserted, removed, and cleaned without the assistance of a health or medical practitioner. The present invention provides a new and novel pessary device that improves the ease of removal of the pessary for both patients and practitioners. The pessary of the present invention includes a unique easy-to-access loop on a stem of the pessary that can fit a finger therein. The loop can be easily located by a patient so they can insert their finger therein so they may pull down on the stem to, in turn, remove the pessary. The removal loop does not rely on pinch strength for pessary removal.

The loop additionally allows practitioners to more easily locate the removal point for the pessary and eliminates the need for forceps or additional tools. The soft, silicone loop decreases the amount of pressure to the vaginal canal because of its flexible, deformable structure. This is unlike the knob on a prior art Gellhorn pessary stem that commonly applies an uncomfortable amount of pressure to the vaginal canal.

Due to typical older demographic of pessary wearers, many suffer from osteoarthritis and limited dexterity. These users are particularly in need of assistance with the removal of their pessary device when self-managing the device on their own. Thus, the unique removal features of the present invention are particularly helpful for these older pessary wearers.

Therefore, the present invention provides a pessary device that is more easily removable. The present invention provides a pessary device that can be managed by the wearer themselves. The present invention provides a pessary device that does not suffer from the disadvantages in the prior art.

BRIEF DESCRIPTION OF THE DRAWING FIGURES

The novel features which are characteristic of the present invention are set forth in the appended claims. However, the invention's preferred embodiments, together with further objects and attendant advantages, will be best understood by reference to the following detailed description taken in connection with the accompanying drawings in which:

Figure 5A:
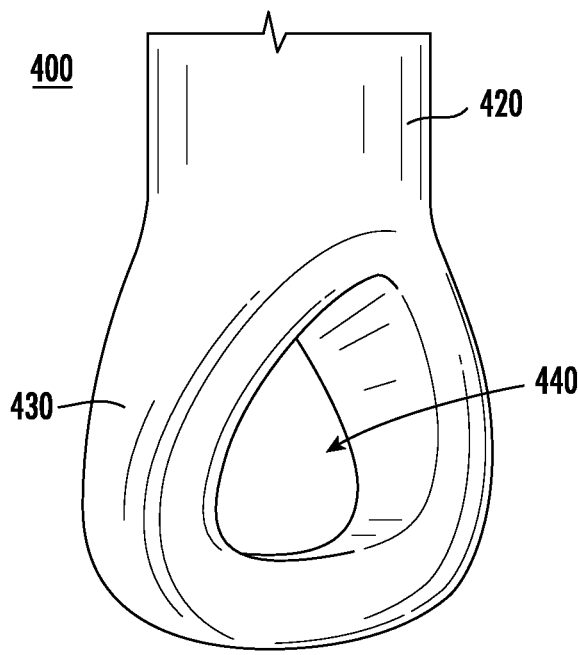
Figure 5B:
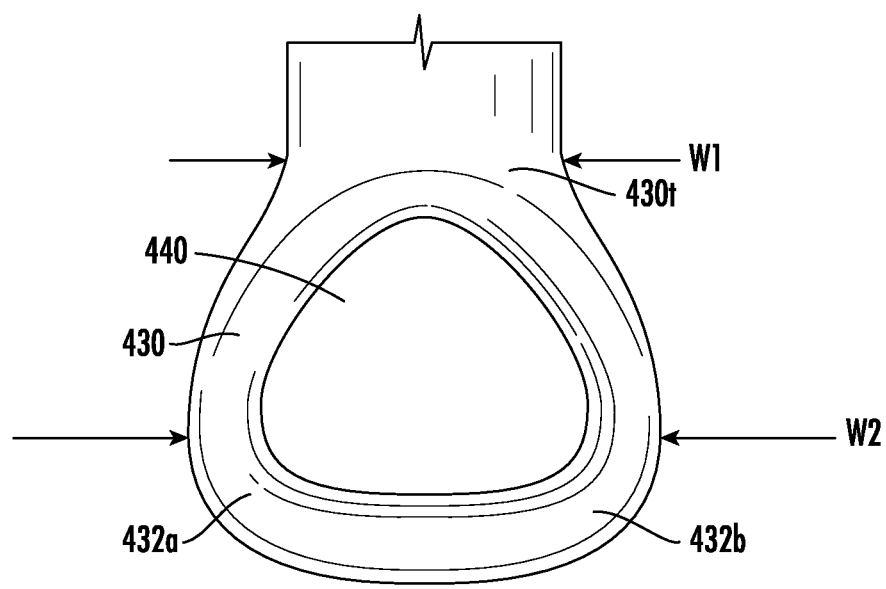
Figure 5C:
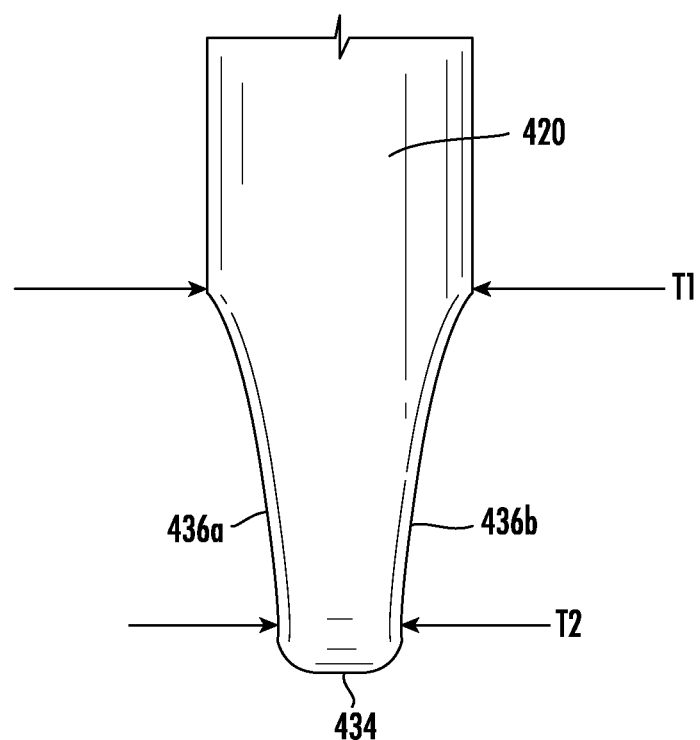
Figure 6A:
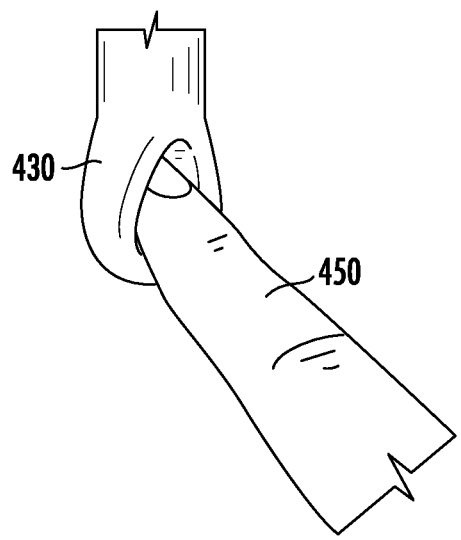
Figure 6B:
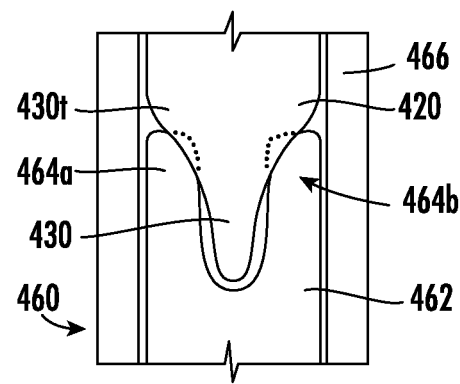
Figure 7A:
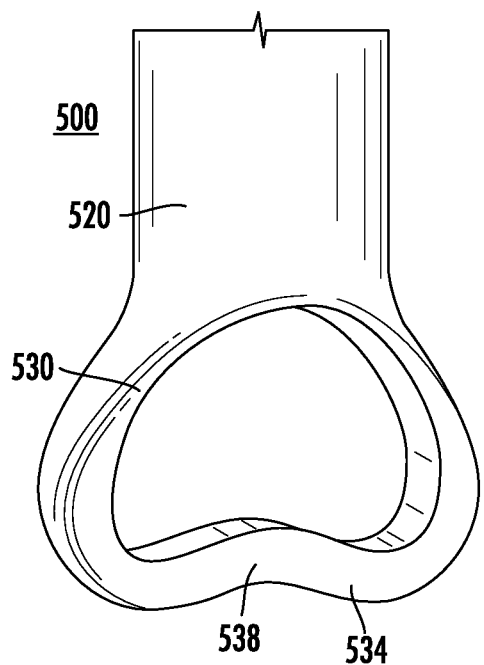
Figure 7B:
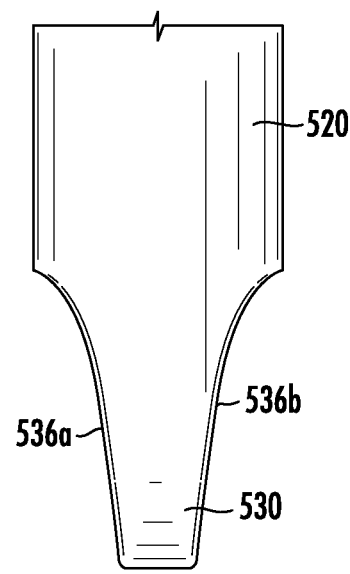
Figure 7C:
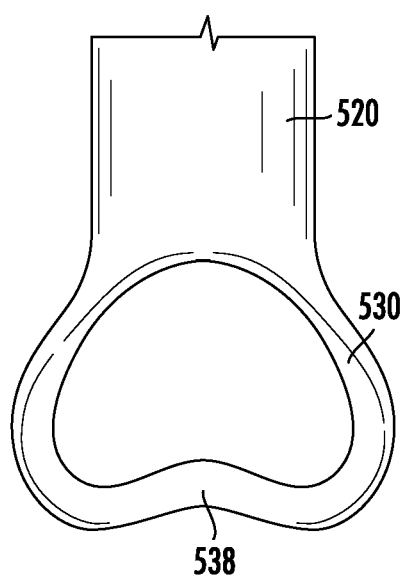
Figure 8:
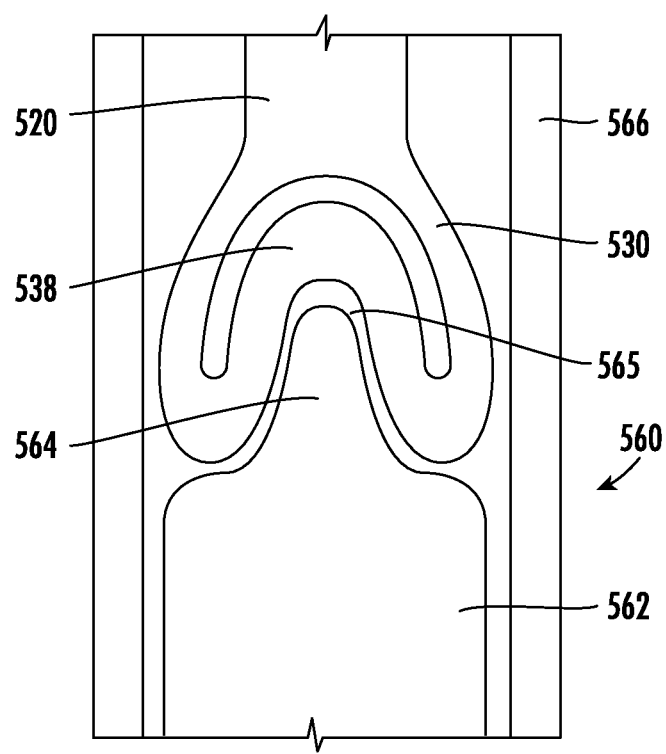
Figure 9A:
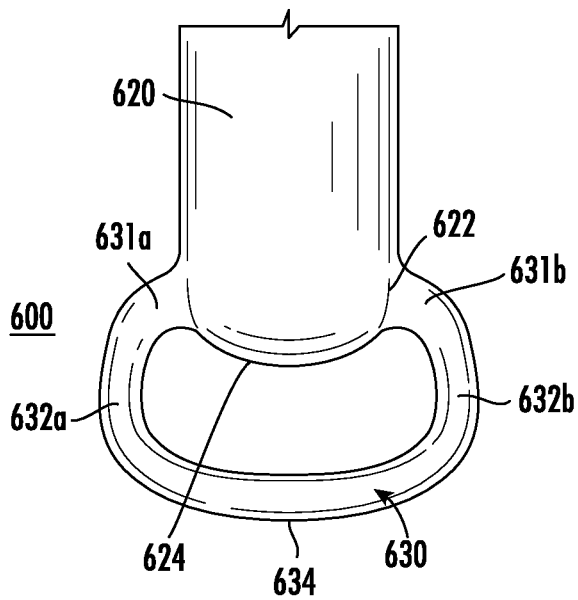
Figure 9B:
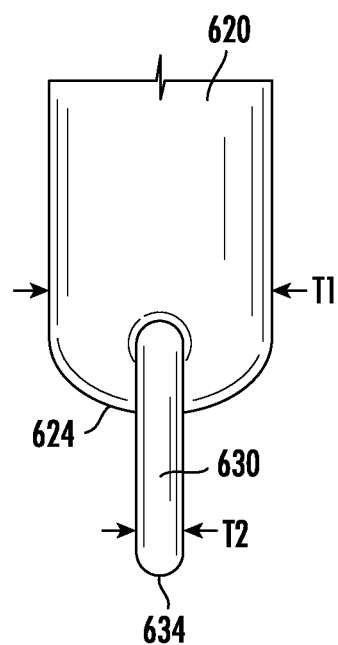
Figure 9C:
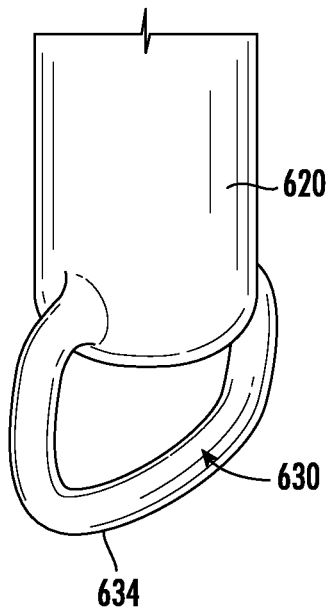

FIGS. 5A-C show another alternative embodiment of the pessary device of the present invention;

FIGS. 6A-B show the pessary device of the present invention in use;

FIGS. 7A-C show another alternative embodiment of the pessary device of the present invention; and FIG. 8 shows the pessary device of the present invention during insertion using an applicator; and FIGS. 9A-9C shows yet a further alternative embodiment of the pessary device of the present invention.

DESCRIPTION OF THE INVENTION

Certain exemplary embodiments will now be described to provide an overall understanding of the principles of the structure, function, manufacture, and use of the device and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present disclosure. Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Further, to the extent that directional terms like top, bottom, up, or down are used, they are not intended to limit the systems, devices, and methods disclosed herein. A person skilled in the art will recognize that these terms are merely relative to the system and device being discussed and are not universal.

Figure 1:
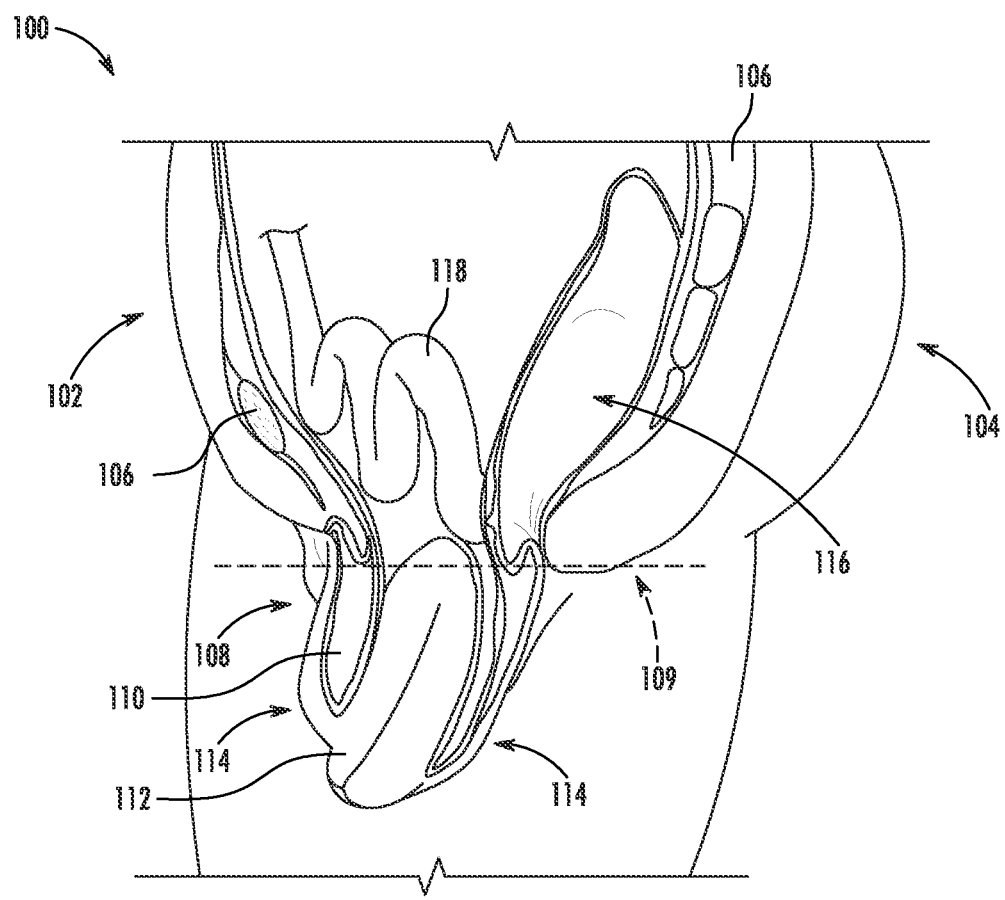
FIG. 1 is a cross sectional view of the pelvic organs in a prolapsed state, according to the prior art.
Figure 2A:
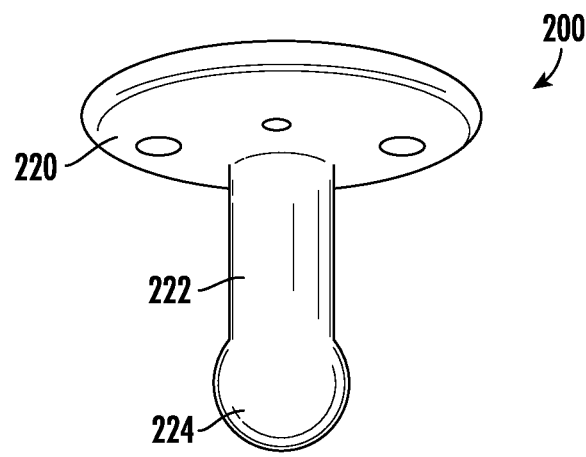
FIGS. 2A and 2B show a prior art pessary device.
Figure 2B:
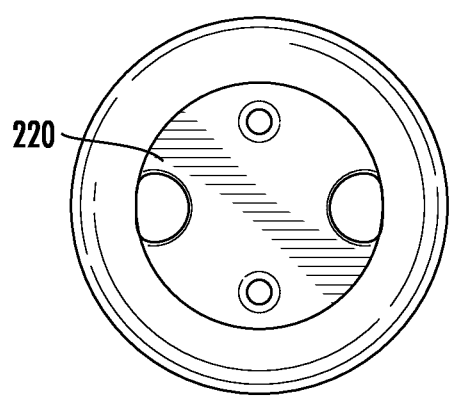
Figure 3:
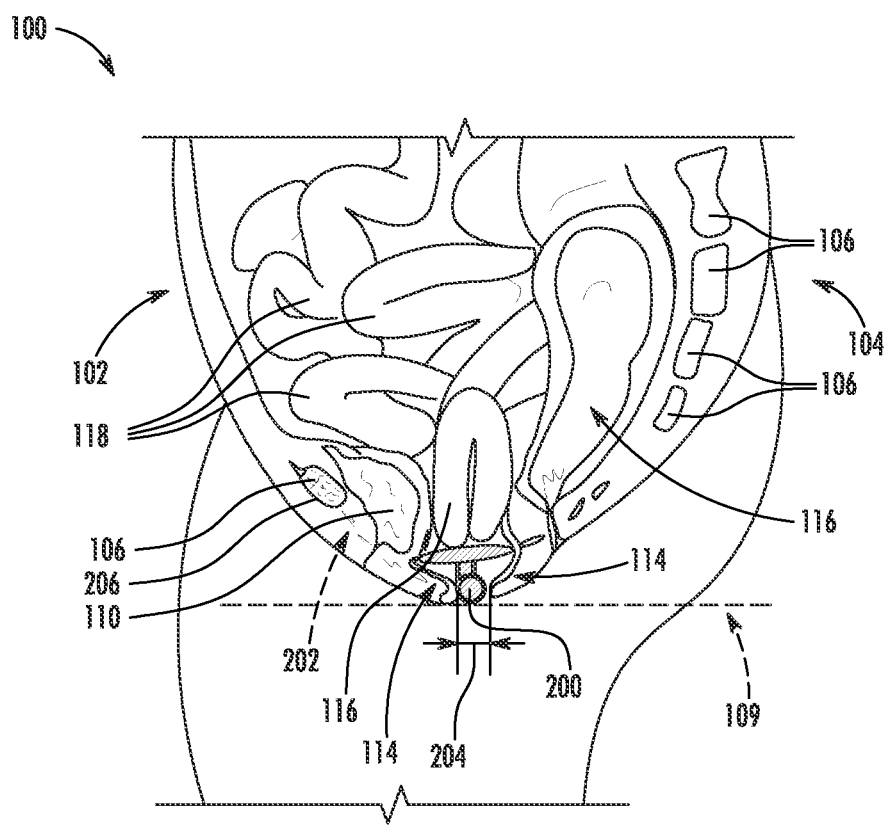
FIG. 3 shows the prior art pessary device of FIGS. 2A and 2B inserted in a user.
Figure 4A:
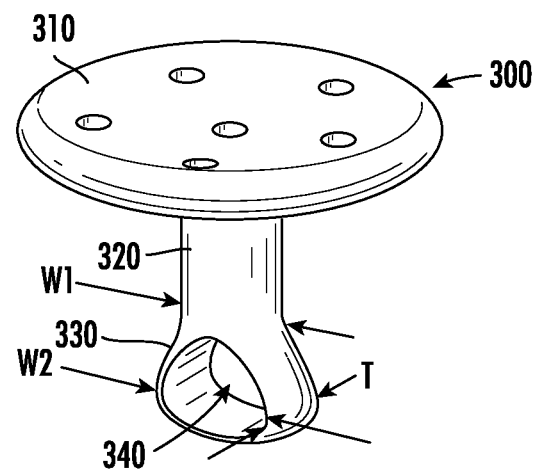
FIGS. 4A and 4B show a first preferred embodiment of the pessary device of the present invention.
Figure 4B:
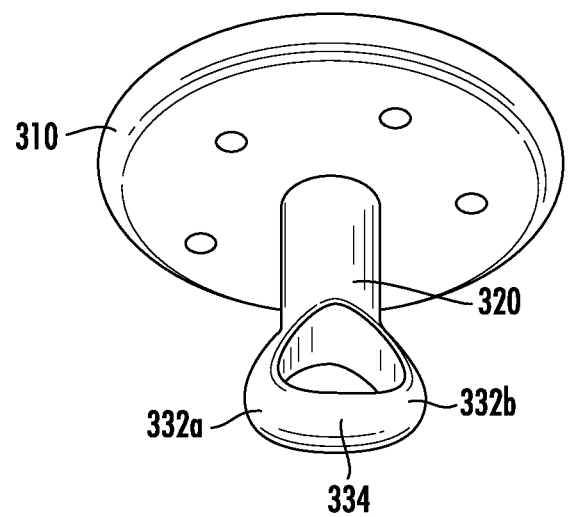

In accordance with an embodiment of the present invention, a new and novel pessary device of the present invention facilitates the removal of pessary devices. A first preferred embodiment of the pessary device 300 according to the present invention is illustrated in FIGS. 4A and 4B. The pessary device 300 of the present invention generally includes a support portion 310, a stem 320, and a loop member, or loop, 330 at the opposite end of a pessary stem from the support portion 310.

While it is preferred that the pessary of the present invention includes a supportive portion 310, a stem 320, and a loop 330, it should be understood that the sizing and dimensions of each of the components of the pessary of the present invention may be modified to suit the patient at hand. For example, the stem 320 may be of any length, where it is made longer, shorter, or even eliminated completely with a length of zero where the loop is attached directly to the supportive portion, which may be appropriate for a given patient. Also, the size and shape of the supportive portion 310 and loop 330 may also be modified and still be within the scope of the present invention.

The novel loop member 330 is provided to facilitate removal of the device from the user 100. In one embodiment, the pessary device 300 can be made, or molded, from medical grade silicone, or other flexible medical grade materials, as a single unitary piece. In another embodiment, the pessary device 300 can be made, or molded, from a medical grade plastic, or other rigid medical grade materials, as a single unitary piece. In other alternative embodiments, the pessary device 300 can be made from a plurality of materials; for example, the support portion 310 and the stem 320 can be made from a more rigid material while the loop is made from a more flexible material like silicone. The loop 330 can be manufactured from soft, or flexible, materials to minimize erosion of tissue in the body and to aid in the insertion and removal of the pessary device 300 into a user 100. In this first embodiment of FIGS. 4A and 4B, the loop 330 preferably extends downward from the stem 320 and has a generally triangular shape with two rounded lower corners 332*a*, 332*b*. The loop 330 extends from a width W1, proximate the stem 320, to a width W2, proximate to the two rounded corners 332*a*, 332*b*. In the illustrated pessary 300, the thickness T of the loop 330 is the same as the thickness of the stem 320.

The loop member 330 can additionally define a through hole 340 which has a generally triangular shape with rounded corners. The through hole 340 can be sized to receive a finger of a user for removal of the pessary 300 from a patient. The lower side 334 of the loop 330 can, in some embodiments, be flexible to minimize erosion of tissue in the body and so that it can be easily bent during insertion. The present disclosure contemplates some alternatives and additions to the loop 330 of the pessary 300 of the present invention. For example, hole 340 can be of any shape, size, or configuration.

Details concerning the support member and stem of the prior art is very well known in the prior art and need not be discussed in detail herein. Therefore, the discussion herein is directed to the novel loop member, removal loop, or loop structure of the present invention that is used as a removal interface.

Turning now to FIGS. 5A-C, an alternative embodiment 400 of the loop 430 in accordance with the present invention is shown. As the stem and support member is the same as the first embodiment 300, they are not shown. In this embodiment 400, the loop 430 is similarly generally triangular shaped as the loop 330. The loop 430 can have a first width W1 proximate the stem 420, or top 430*t* of the loop, and a larger width W2 proximate two rounded corners 432*a*, 432*b*. The lower face, or side, 434 of the loop 430 can be flexible or bendable.

The embodiment 400 of FIGS. 5A-C, in contrast to the embodiment 300 of FIG. 4A-B, includes a tapered loop on opposing sides 436*a*, 436*b* where the thickness T of the loop decreases so the more rigid underside of the stem 420 can be more easily accessed if the entire pessary device needs to be pushed up higher into the vagina. The loop 430 is tapered so that it has a thinner thickness T2 at a lower end of the loop than at the top of the loop 430*t*, where it has a thickness T1. In the illustrated embodiment the thickness T1 can be the same as the thickness of the stem from the side view, as seen in FIG. 5C. The tapered geometry of the two sides 436*a*, 436*b* can be defined by a plane that extends perpendicular to the through hole of the loop. The tapered geometry can follow a parabolic line, as shown in FIG. 5C, so that it is partially concavely curved. Alternatively, the tapered geometry of the two sides 436*a*, 436*b* can be an angled flat line or other geometry and still be within the scope of the present invention. The tapered geometry can allow for easier access to the bottom of the stem 420 so that the bottom of the stem can be located and accessed with a finger 450, as in FIG. 6A, or applicator 460 or other insertion accessory, as in FIG. 6B.

In the event that the entire pessary needs to be pushed up higher into the vagina during insertion, the user or medical practitioner can more easily locate the stem 420. In use, for example, FIG. 6A shows a finger accessing and engaging with the loop for better access and control of the pessary device.

FIG. 6B shows the use of an applicator 460 including a plunger 462 and surrounding applicator housing 466. The housing 466 can be tubular and can have a cross section that is substantially the same geometry as the cross sectional geometry of the loop 430. The plunger 462 preferably has a generally forked shape, having two prongs 464a, 464b that are configured for engagement with the tapered geometry of the tapered shape of the loop 430 of the pessary, such as in FIGS. 5A-5C. The tapered geometry allows the two prongs 464a, 464b to access and engage the bottom of the stem 420, or the top of the loop 430t. Therefore, the two prongs 464a, 464b are able to push, or apply a force, to the more rigid stem 420 of the pessary to allow for the pessary to be moved into the proper location.

The unique shape of the removal loop 430 being more triangular with it tapering at the top 430t and widening at the bottom 434, can allow for easier location of the loop 430 by a finger 450 for pulling during removal and for easier location of the top of the loop 430t or the bottom of the stem 420 to push the entire pessary up higher into the vagina during insertion. The flatter bottom 434 of the loop 430 can increase contact between the finger 450 and the loop 430 during removal. The geometry of the loop 430 helps to distribute forces from a finger 450 or tool 460 pulling the loop during removal to minimize risk of the loop 430 tearing. While maintaining flexibility, the geometry of the loop 430 can be substantial enough to prevent tearing and excessive wear.

The loop 430 can be flexible to minimize development of vaginal sores and ulcers. The flexibility will prevent the removal feature from acting as a single pressure point, a cause of vaginal ulcers, and in extreme cases, fistulas by deforming to minimize the pressure.

The removal loop feature, or loop, 430 is also flexible so that it can more easily fit inside of an applicator. If an applicator 460 is used to aid in the insertion of the pessary, the loop 430 can flex to better conform to the shape of the applicator, either the body of the applicator, plunger of the applicator or both. For example, if the body 466 of the applicator 460 was the same width as the rest of the stem 420, the removal feature is flexible to conform to that width.

FIGS. 7A-7C show another alternative embodiment 500 of the loop portion 530 of a pessary of the present invention. In this embodiment, similar to the embodiment of FIGS. 5A-C, a tapered loop 530 may be provided where the thickness T of the loop 530 is tapered, on sides 536a, 536b, so the rigid part of the stem 520 can be more easily accessed if the entire pessary needs to be pushed up higher into the vagina. This tapering is similar to the embodiment 400, thus only the dimple 538 structure is discussed herein. The loop 530 in the embodiment of FIGS. 7A-C also includes an inwardly facing dimple 538 in the bottom of the loop 534 so that it can collapse in a more controlled fashion if the bottom 534 of the loop 530 is pushed upwardly. The dimple 538 can function as a compliant hinge to permit controlled bending of the bottom arm 534. For example, as in FIG. 8, an applicator 560 can include a plunger 562 disposed within a plunger housing 566. The plunger 562 can include a single prong 564 having a ridged contact face 565 that is configured and well-suited for interfacing with the dimple 538 of the loop 530 of FIGS. 7A-C. In this embodiment, during insertion, the loop deforms for better control and application of force on the stem 520 with the assistance of dimple 534.

The shape of the loop, or removal feature, in the embodiments of FIGS. 4A-B, 5A-C, and 7A-C is generally triangular with it tapering at the top and widening at the bottom. The triangular shaped loops 330, 430, 530 can both allow for easier location of the loop by a finger for pulling during removal and for easier location of the top of the loop/bottom of the stem to push the entire pessary up higher into the vagina during insertion. The flatter bottom side of the respective loops 334, 434, 534 can increase contact between the finger and the loop during removal. The geometry of the loop can be designed to distribute forces from a finger or tool pulling the loop during removal to minimize risk of tearing. Alternatively, it should be noted that any other shape may be employed in accordance with the present invention, such as shapes that are non-triangular. For example, FIGS. 9A-C illustrate such an alternative embodiment of the present invention.

In the further embodiment of FIGS. 9A-C, a non-triangular shaped loop embodiment 600 is shown. This alternative embodiment provides a thin loop 630 of material where the rigid part of the stem 620 is very easy to access and is more pronounced and bulbous compared to the other embodiments of the loops of the present invention. This is achieved by a rectangular, or oval, or other shaped loop 630 that has a thickness T2 that is smaller than the thickness T1 of the stem 620. The loop 630 can have first portions 631a, 631b that extend from the stem 620 at a height 622 that is above the bottom most end 624 of the stem in a radially outward direction from the stem 620. The first part 631a,b of the loop 630 can then extend downward forming two arms 632a, 632b which are connected by a bottom side 634. The smaller thickness T2 of the loop 630 can allow for easier identification of the stem 620, which has a larger thickness T1, for positioning purposes. This embodiment 600 additionally allows for the bottom of the stem 624 to act as an anchor against the vaginal walls and prevent the pessary from flipping upside down in the vaginal canal.

The pessary device, according to any of the embodiments, can be made of known materials that are suitable for pessary devices, such as silicone with or without inserts made of nylon or other rigid material. Such inserts are configured to prevent the loop from being too stretchy or to minimize the possibility of tearing. The removal feature can also be made out of silicone that is a different durometer from the supportive portion of the pessary to either increase rigidity or flexibility of the removal feature. Any of the described removal features can be applied to any stem length, even a stem length of zero where the loop is attached directly to the bottom of the supportive portion, to suit the patient or treatment protocol.

It would be appreciated by those skilled in the art that various changes and modifications can be made to the illustrated embodiments without departing from the spirit of the present invention. All such modifications and changes are intended to be covered by the appended claims.

What is claimed is:

1. A removable pessary device for insertion into the vagina, comprising:
   a supportive portion;
   a stem, having a first end and a second end, the first end connected to the supportive portion; and
   a loop, having a hole extending therethrough and a free end, connected to the second end of the stem; the loop having walls, each wall being defined by a plane that extends perpendicular to the hole of the loop;

wherein the walls taper inwardly from the second end of the stem toward the free end of the loop;
wherein the loop facilitates manipulation of the removable pessary device.

2. The removable pessary device of claim 1, wherein the loop is flexible or rigid.

3. The removable pessary device of claim 2, wherein the free end of the loop includes a dimple to facilitate deformation of the loop.

4. The removable pessary device of claim 1, wherein a width at the free end of the loop is greater than a width of the stem.

5. The removable pessary device of claim 1, wherein the removable pessary is constructed from a plurality of different materials.

6. The removable pessary device of claim 1, wherein the tapered walls are tapered along a curved line from the second end of the stem to the free end of the loop.

7. The removable pessary device of claim 1, wherein a thickness of the entire loop is less than a thickness of the stem.

8. The removable pessary device of claim 1, wherein the loop is triangular.

9. The removable pessary device of claim 1, wherein the removable pessary device is made of a silicone material.

10. The removable pessary device of claim 9, wherein the loop is made of a silicone material having a different durometer from the supportive portion.

11. A removable pessary device for insertion into the vagina, comprising:
a supportive portion; and
a loop, having a hole extending therethrough and a free end, connected to the supportive portion; the loop having walls, each wall being defined by a plane that extends perpendicular to the hole of the loop;
wherein the walls taper inwardly from the second end of the stem toward the free end of the loop;
wherein the loop facilitates manipulation of the removable pessary device.

12. The removable pessary device of claim 11, wherein the loop is flexible or rigid.

13. The removable pessary device of claim 12, wherein the free end of the loop includes a dimple to facilitate deformation of the loop.

14. The removable pessary device of claim 11, wherein the removable pessary is constructed from a plurality of different materials.

15. The removable pessary device of claim 11, wherein the removable pessary device is made of a silicone material.

16. The removable pessary device of claim 15, wherein the loop is made of a silicone material having a different durometer from the supportive portion.

17. The removable pessary device of claim 11, wherein the loop is triangular.

18. The removable pessary device of claim 11, wherein the tapered walls are tapered along a curved line.

19. A removable pessary system, the system comprising,
a removable pessary for insertion into the vagina, including,
a supportive portion;
a stem, having a first end and a second end, the first end connected to the supportive portion; and
a loop, having a hole extending therethrough and a free end, connected to the second end of the stem; the loop having walls, each wall being defined by a plane that extends perpendicular to the hole of the loop;
wherein the walls taper inwardly from the second end of the stem toward the free end of the loop; and
an applicator including,
a housing, and
a plunger telescopically received in the housing,
wherein the removable pessary is received in the applicator.

20. The removable pessary system of claim 19, wherein the plunger is configured to apply a force to a distal most end of the stem.

21. The removable pessary system of claim 19, wherein the plunger includes a distal end having a forked structure to receive a lower most end of the loop.

22. The removable pessary system of claim 19, wherein the tapered walls are tapered along a curved line from the second end of the stem to the free end of the loop.

23. The removable pessary system of claim 19, wherein the loop is flexible and the free end of the loop includes an upward extending dimple to facilitate deformation of the loop.

24. The removable pessary system of claim 23, wherein the plunger includes a distal end having a single prong configured to engage the dimple to deform the loop.

25. A removable pessary system, the system comprising,
a removable pessary for insertion into the vagina, including,
a supportive portion; and
a loop, having a hole extending therethrough and a free end, connected to the supportive portion; the loop having walls, each wall being defined by a plane that extends perpendicular to the hole of the loop;
wherein the walls taper inwardly from the second end of the stem toward the free end of the loop; and
an applicator including,
a housing, and
a plunger telescopically received in the housing,
wherein the removable pessary is received in the applicator.

26. The removable pessary system of claim 25, wherein the plunger is configured to apply a force to a distal most end of the loop.

27. The removable pessary system of claim 25, wherein the plunger includes a distal end having a forked structure to receive a lower most end of the loop.

28. The removable pessary system of claim 25, wherein the tapered walls are tapered along a curved line.

29. The removable pessary system of claim 25, wherein the loop is flexible and the free end of the loop includes an upward extending dimple to facilitate deformation of the loop.

30. The removable pessary system of claim 29, wherein the plunger includes a distal end having a single prong configured to engage the dimple to deform the loop.

* * * * *